United States Patent [19]

Neilson

[11] 3,940,692
[45] Feb. 24, 1976

[54] APPARATUS FOR MONITORING RECURRENT WAVEFORMS

[75] Inventor: James McEwan McIntyre Neilson, Edinburgh, Scotland

[73] Assignee: The University of Edinburgh, Edinburgh, Scotland; a part interest

[22] Filed: Dec. 14, 1973

[21] Appl. No.: 424,815

[30] Foreign Application Priority Data
Dec. 15, 1972 United Kingdom............... 48106/72

[52] U.S. Cl............................ 324/77 R; 128/2.06 A
[51] Int. Cl.² ........................................ G01R 23/16
[58] Field of Search...... 324/77 R, 77 B, 77 D, 102; 128/2.06 F, 2.05 T, 2.06 R, 2.06 A

[56] References Cited

UNITED STATES PATENTS 3,829,766    8/1974    Herz.................................. 324/77 R

FOREIGN PATENTS OR APPLICATIONS 1,282,051    7/1972    United Kingdom............... 324/77 R Primary Examiner—R. V. Rolinec
Assistant Examiner—Ernest F. Karlsen
Attorney, Agent, or Firm—Woodhams, Blanchard and Flynn

[57] ABSTRACT

A method and apparatus for monitoring recurrent waveforms such as electrocardiogram (e.c.g.) waveforms. The e.c.g. apparatus comprises integrators and stores for storing integrated segments of a normal, reference waveform complex. A timing circuit derives timing signals from the e.c.g. waveform to be monitored. The timing signals represent the time location of particular selected parts of the waveform which are to be compared with the corresponding parts of the stored waveform. The e.c.g. waveform is corrected by subtracting a version of the waveform after it has passed through a low pass filter from a delayed version. Corrected segments of the waveform are integrated and subtracted from the corresponding stored segments of the reference waveform to provide a difference signal and the difference signals are quantitatively summed. An output signal is produced if the total sum of the magnitudes of the difference signals exceeds a predetermined value to indicate an abnormal complex.

33 Claims, 13 Drawing Figures

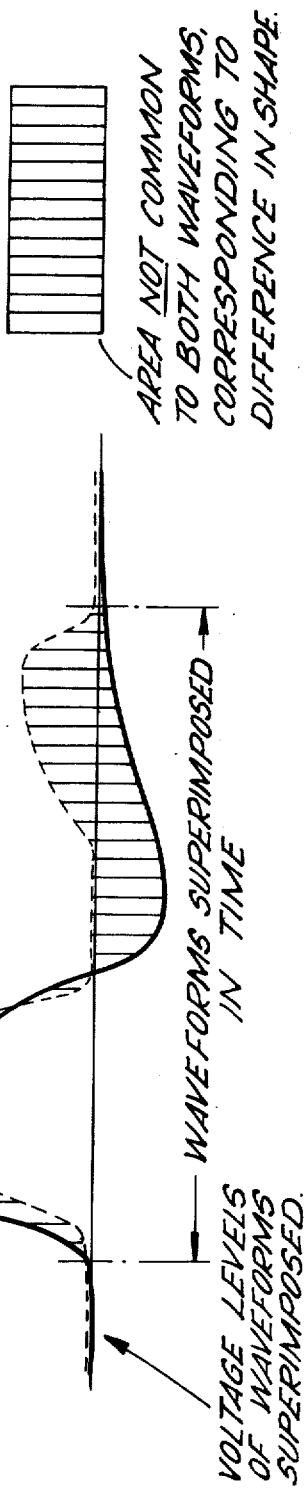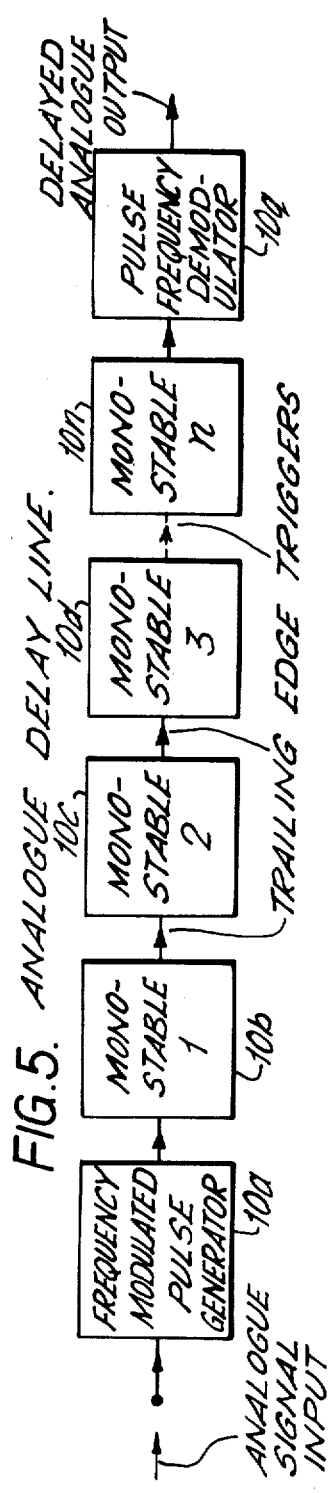

APPARATUS FOR MONITORING RECURRENT WAVEFORMS

The invention relates to a method of and apparatus for monitoring recurrent waveforms.

The invention has an important application in apparatus for monitoring electrocardiogram waveforms, hereinafter also referred to as e.c.g. waveforms.

It is frequently necessary to monitor such recurrent waveforms to detect abnormal complexes, for instance it is necessary to detect ventricular ectopic complexes in electrocardiogram waveforms. It is known that such complexes exhibit a difference in shape as compared with normal complexes. Such abnormal complexes are also referred to herein as "foreign" complexes.

In the complete specification of our British Pat. No. 1,282,051 there was disclosed a method of monitoring a recurrent waveform to detect abnormal waveform complexes comprising the steps of integrating successive segments of a waveform complex, determining the difference between the integrated value of each segment in the complex with the integrated value of a corresponding segment of a normal waveform complex to provide a difference signal, quantitatively summing the difference signals and producing a signal and/or record if the total sum of the difference signals exceed a predetermined value to indicate an abnormal complex.

There was also disclosed apparatus for monitoring recurrent waveforms to detect abnormal waveform complexes in said recurrent waveform comprising means for integrating successive segments of a waveform complex, means for determining the difference between the integrated value of each segment and that of the corresponding segment of a normal complex, means for adding the magnitudes of said differences irrespective of sign to determine the resultant difference, and means for indicating whether the magnitude of said resulting difference indicates an abnormal complex.

The present invention represents an improvement in or modification of the invention of our earlier patent.

According to the present invention in one aspect there is provided a method of monitoring a recurrent waveform to detect abnormal waveform complexes comprising the steps of integrating successive segments of a waveform complex, determining the difference between the integrated value of each segment in the complex with the integrated values of corresponding segments of $(p + 1)$ different normal waveform complexes, where $p$ is an integer to provide $(p + 1)$ sets of difference signals, quantitatively summing the difference signals associated with each normal waveform and producing a signal and/or record to indicate an abnormal complex if the total sum of the magnitudes of the difference signals associated with a first normal waveform complex exceeds a first predetermined threshold level and the sums of the magnitudes of the $p$ other difference signals are not less than a second predetermined threshold level for each of the $p$ other normal waveform complexes.

The threshold levels may be the same or different. The threshold levels are adaptive in so far as they are derived from variables.

The method according to the first aspect may further comprise the step of producing a second signal and/or record if one of the sums of the magnitudes of the difference signals is less than its associated predetermined threshold level, the signal and/or record being arranged to indicate that the monitored waveform is a normal waveform and to which of the $(p + 1)$ normal waveforms it corresponds.

Each threshold level may be derived from a voltage dependent upon the total area of the corresponding normal complex, the high frequency and low frequency contents of the signal to be monitored and a fixed, d.c. level.

Thus one criterion in the detection of an abnormal complex is the signal to noise ratio prevailing when the complex appears.

Preferably the difference between the integrated value of each segment in the complex of the waveform to be monitored and the corresponding segments of the $(p + 1)$ normal waveforms is determined simultaneously.

In a development of the invention a signal and/or record is produced to indicate an abnormal complex if the sum of the magnitudes of the difference signals associated with all of the normal waveform complexes exceed predetermined threshold values.

The method may further comprise the step of producing further signals and/or records if one or more of the sums of the magnitudes of the difference signals is less than another associated predetermined (i.e. Normal threshold) threshold level, the signal(s) and/or record(s) being arranged to indicate that the monitored waveform is a normal waveform and to which of the $(p + 1)$ normal waveforms it corresponds.

According to the present invention in a second aspect there is provided a method of monitoring a recurrent waveform to detect abnormal waveform complexes comprising the steps of integrating and storing segments of a normal waveform complex to be used as a reference, integrating successive segments of a waveform complex, deriving from the recurrent waveform timing signals which represent the time location of particular selected parts of the waveform complex required to be compared with the integrated value of corresponding parts of the stored normal complex, deriving a correcting signal by filtering the waveform to be monitored by passing it through a low-pass filter to provide a baseline signal, delaying the waveform, subtracting said correcting signal from said delayed waveform to provide a corrected waveform, determining, with the aid of the timing signals, the difference between the integrated value of each segment in the corrected complex and the integrated value of a corresponding segment of the normal waveform complex to provide a difference signal, quantitatively summing the difference signals and producing a signal and/or record if the total sum of the magnitudes of the difference signals exceed a predetermined value to indicate an abnormal complex.

Preferably the corrected waveform is filtered by passing it through a high-pass filter before the step of determining the difference between the integrated value of each segment in the corrected complex and the integrated value of a corresponding segment of the normal waveform.

The timing signals may be derived from the waveform by high-pass filtering, rectification, smoothing, differentiating twice the smoothed signal in that order, and comparing the second derivative signal with a threshold derived by separately high-pass filtering and smoothing the high frequency noise components of the recurrent waveform to be monitored to provide an output signal when the second derivative signal exceeds the threshold signal.

Preferably, the first derivative signal is compared with a reference level (such as zero volts) to provide a signal when it is equal to the reference level, and the signal is applied to a monostable circuit for generating at its output a pulse of predetermined time duration and having a fixed time relationship to the "centre" of that part of the waveform complex to be compared with the reference complex, and the output signal of the preceding paragraph is added to the pulse from the monostable circuit in an AND-gate to provide a trigger signal, that is a timing signal.

The method of the first and second aspects of the invention may be combined.

Preferably the integration of corresponding segments of the or each normal waveform complex to be stored and the waveform complex to be compared with it is successive and carried out by operational amplifiers electronically switched under the control of the timing signal.

The operational amplifier stages may be arranged to obtain the differences between each integrated segment of the waveform complex and that of each stored reference waveform complex and to obtain the sum of the magnitudes of said individual differences over a time interval including the start of the waveform complex and the end of the widest expected waveform complex.

According to a third aspect of the invention there is provided apparatus for monitoring recurrent waveforms to detect abnormal waveform complexes in said recurrent waveform comprising means for integrating successive segments of a waveform complex, means for determining the difference between the integrated value of each segment in the complex and the integrated values of the corresponding segments of $(p + 1)$ different normal waveform complexes, where $p$ is an integer, to provide $(p + 1)$ sets of difference signals means for adding the magnitudes of said difference signals associated with each normal waveform irrespective of sign, and means for indicating an abnormal complex if the total sum of the magnitudes of the difference signals associated with a first normal waveform complex exceeds a first predetermined threshold level and the sums of the magnitudes of the $p$ other difference signals are not less than a second predetermined threshold level for each of the $p$ other normal complexes.

The apparatus may further comprise means for indicating a normal complex if one of the sums of the magnitudes of the difference signals is less than an associated predetermined threshold level and for indicating to which of the $(p + 1)$ normal waveforms it corresponds.

The threshold levels may be the same or different. The threshold levels are adaptive in so far as they are derived from variables.

Each threshold level may be derived from a voltage dependent upon the total area of the corresponding normal complex, the high frequency and low frequency contents of the signal to be monitored and a fixed, d.c. level.

Preferably the difference between the integrated value of each segment in the complex of the waveform to be monitored and the corresponding segments of the $(p + 1)$ normal waveforms is determined simultaneously.

In a development of the apparatus according to the invention, the indicating means is arranged to provide an indication of an abnormal complex if the sums of the magnitudes of the difference signals associated with all of the normal waveform complexes exceed predetermined threshold values.

According to the present invention in a fourth aspect there is provided apparatus for monitoring a recurrent waveform to detect abnormal waveform complexes comprising means for integrating and storing segments of a normal waveform complex to be used as a reference, means for integrating succesive segments of a waveform complex to be monitored, means for deriving from the recurrent waveform timing signals which represent the time location of particular selected parts of the waveform complex required to be compared with the integrated value of corresponding parts of the stored normal complex, means for deriving a correcting signal, including means for filtering the waveform to be monitored by passing it through a low-pass filter to provide a baseline signal, means for delaying the waveform, means for subtracting said correcting signal from said delayed waveform to provide a corrected waveform, means for determining, with the aid of the timing signals, the difference between the integrated value of each segment in the corrected complex and the integrated value of a corresponding segment of the normal waveform complex to provide a difference signal, means for quantitatively summing the difference signals and for producing a signal and/or record if the total sum of the magnitudes of the difference signals exceed a predetermined value to indicate an abnormal complex.

Preferably the apparatus comprises means for passing the corrected waveform through a high-pass filter to the means for determining the difference between the integrated value of each segment in the corrected complex and the integrated value of a corresponding segment of the normal waveform.

The means for deriving timing signals may comprise a high-pass filter, a rectifier, smoothing means, means for differentiating twice the smoothed signal coupled together in that order, and means for comparing the second derivative signal with a threshold level derived by a high-pass, filter and smoothing means for filtering and smoothing the high frequency noise components of the recurrent waveform to be monitored to provide an output signal when the second derivative signal exceeds the threshold signal.

Preferably, the means for deriving timing signals comprises means for comparing the first derivative signal with a reference level (such as zero volts) to provide a signal when it is equal to the reference level, and the signal is applied to a monostable circuit for generating at its output a pulse of predetermined time duration and having a fixed time relationship to the "centre" of that part of the waveform complex to be compared with the reference complex, and the output signal of the preceding paragraph is added to the pulse from the monostable circuit in an AND-gate to provide a trigger signal.

The apparatus of the third and fourth aspects of the invention may be combined.

Preferably the integration of corresponding segments of the or each normal waveform complex to be stored and the waveform complex to be compared with it is successive and carried out by operational amplifiers electronically switched under the control of the timing signal.

The operational amplifier stages may be arranged to obtain the differences between each integrated segment of the waveform complex and the or each stored reference waveform complex and to obtain the sums of said individual differences over a time interval including the start of the waveform complex and the end of the widest expected waveform complex.

In apparatus according to the invention arranged to monitor e.c.g. waveforms, the indicating means may be arranged to record and/or indicate different disturbances of the heart rhythm of a patent, such as ventricular tachycardia and may further be arranged to operate individual alarms specific to the condition detected.

The invention will now be described by way of example with reference to the accompanying drawings, in which:

FIG. 3 shows graphically a sample complex and a normal complex, plotted on the same scales;

FIG. 5 shows in greater detail an example of a delay line suitable for use in the apparatus of FIG. 4;

Figure 1:
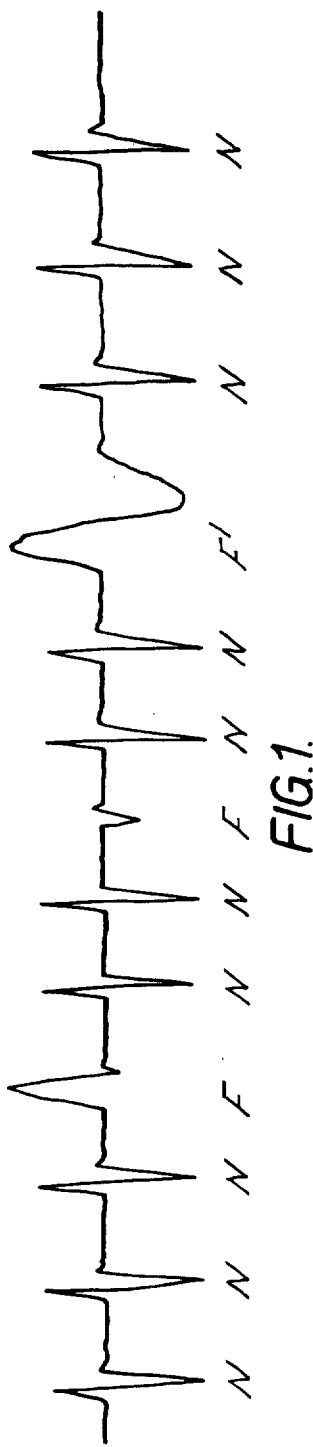
FIG. 1 shows an example of a recurrent waveform to which the invention is applicable.

The invention is applicable, generally to a waveform consisting of a train of essentially similar transients such as those marked N in FIG. 1, so as to detect the presence and time of occurrence of individual transients in the train, such as those marked F and F' in FIG. 1, which are appreciably different in shape from that of the prevailing transients N.

Figure 2:
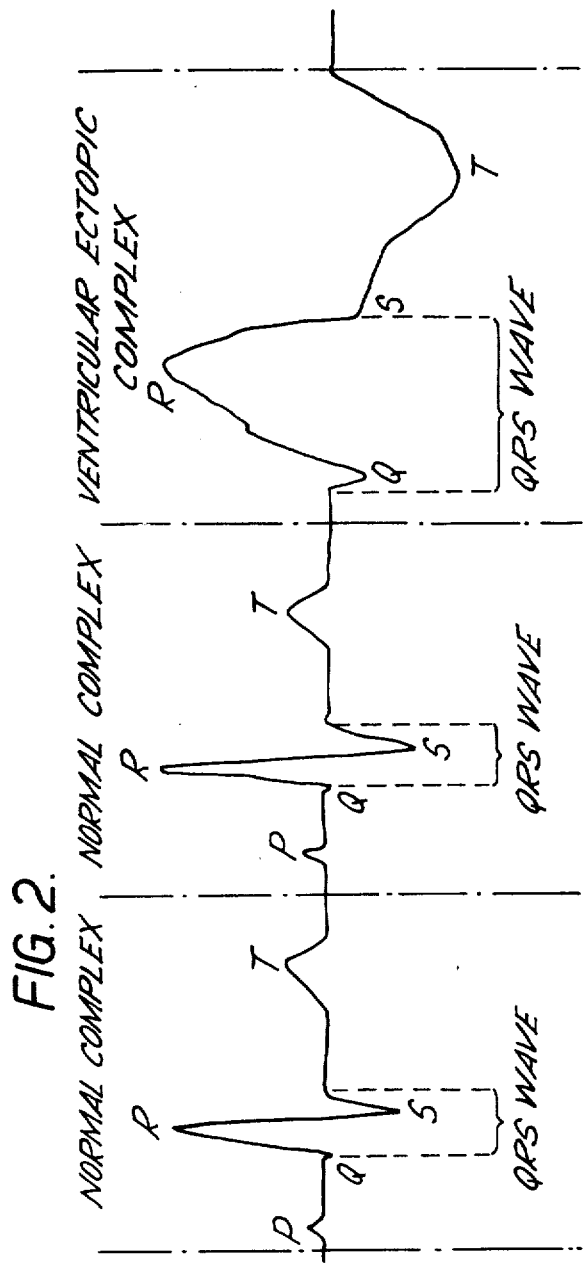
FIG. 2 is an enlarged view of three cycles of the waveform illustrating a foreign complex.

Referring to FIGS. 2 and 3, these illustrate the application of the invention to the particular problem of monitoring electrocardiogram (e.c.g.) waveforms to detect abnormalities, for example, ventricular ectopic complexes on the basis that these complexes invariably differ in shape from the "normal" e.c.g. complex.

The method and apparatus now to be described makes possible the automatic detection of oddly shaped ('Foreign') complexes in the electrocardiogram, particularly ventricular ectopic complexes.

The method of operation according to the present invention may be described as follows:

Each individual e.c.g. complex is detected (FIG. 8) as it arrives by filtering the incoming signal to emphasise the relatively sharp corners of the QRS waves, rectifying this filtered signal and smoothing the result by a low pass filter, twice differentiating this smoothed signal with respect to time and generating a trigger pulse each time a QRS wave causes this second differential voltage to exceed a trigger threshold proportional to the average high frequency content of the incoming signal. The generation of each trigger pulse is timed to coincide with the peak of the smoothed signal which bears a fixed time relationship to the centre of the QRS wave producing it.

Each individual e.c.g. complex is, in effect, electronically superimposed both in time (using the timed trigger pulses derived from the QRS waves above) and in voltage level (by making all measurements on a corrected version of the incoming e.c.g. signal from which deviations of the baseline have been substantially removed) with a sample of the prevailing normal (A) complex stored within the circuit. Simultaneously, the complex under examination is also effectively superimposed with samples of other normal complexes ('Normal B', 'Normal C' ... ect.) stored within the circuit.

The total area not common to both the stored 'Normal A' sample waveform and that of the complex being examined is calculated (shaded area FIG. 3) and used as a measure of the difference in shape between the current complex and the stored 'normal A' sample. Likewise, in other parts of the circuit the total area not common to the current complex and each of the other stored 'Normal' complexes is calculated and used as measures of the difference in shape between the current complex and each of the alternative stored normal complexes. A voltage proportional to the difference in shape so calculated in respect of each of the stored normal complexes is compared with a threshold voltage for that normal complex derived from a preset combination of voltages proportional to the total area of the stored complex concerned, high frequency content of the incoming signal, the low frequency content of the incoming signal, and a fixed (D.C.) term. The particular combination used may be preset differently for each of the stored normal complexes.

If the difference in shape between the complex under examination and any of the stored normal complexes is less than the (preset adaptive) threshold for that stored normal complex, the presence of a normal complex of that type (A, B, C ... etc.) is detected and an appropriate output produced.

If the difference in shape between the complex under examination and stored normal A complex exceeds another adaptive preset threshold derived from a (generally different) combination of the same components (total area of normal complex A, high and low frequency contents of the incoming signal, and a fixed D.C. term, and if no other normal shape is detected, the complex examined is detected as Foreign and an appropriate output produced.

The detection of a complex of 'Abnormal or Foreign' shape may be used to generate an output from the circuit signifying the detection of a ventricular ectopic complex.

Figure 4:
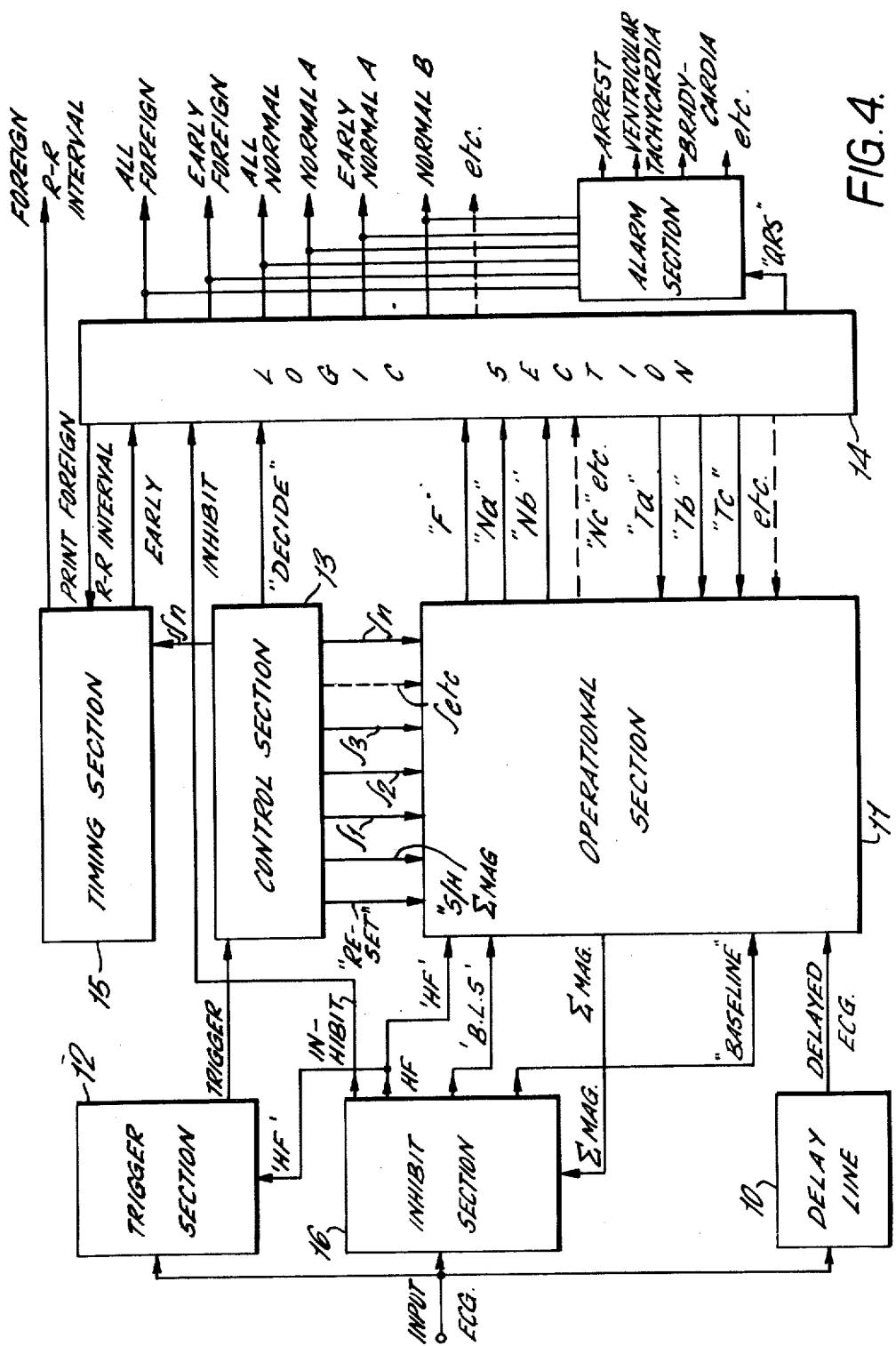
FIG. 4 shows in block form the general arrangement of monitoring apparatus embodying the invention.

The BLOCK DIAGRAM of the system is shown in FIG. 4. The incoming e.c.g. signal is fed through a Delay Line 10 to the Operational Section 11 (FIGS. 6 and 7) in which measurements are made of the shape of the complexes in a corrected version of the delayed replica of the original signal.

Meanwhile the original e.c.g signal is fed to the Trigger Section 12 (FIG. 8) in which the appearance of each QRS wave is detected and used to generate a trigger pulse for each QRS wave detected.

The trigger pulses are fed to the Control Section 13 (FIG. 9) in which a sequence of control pulses is generated and fed to the Operational Section 11 and Logic Section 14 (FIG. 10) initiating and timing the operations carried out in these sections.

In the Operational section 11 electronically switched operational amplifiers integrate successive segments of each corrected, delayed e.c.g. waveform and subtract the areas measured in these segments from the areas of corresponding segments in a sample normal A e.c.g. waveform stored in a set of sample/hold circuits (store A). Other operational amplifiers in this section calculate the sum of the magnitudes of the differences ($\Sigma A$) between corresponding segments in the two complexes and generate logic voltage levels Foreign Shape or Normal A Shape according to whether $\Sigma A$ exceeds or does not reach Foreign or Normal A thresholds each of which adjusts automatically to a preset combination of signals derived from the incoming e.c.g.

Similarly the areas measured in successive segments of each corrected delayed e.c.g. complex are subtracted from the areas of corresponding segments in a sample Normal B e.c.g. waveform stored in a separate set of sample/hold circuits (store B) and further operational amplifiers calculate the sum of the magnitude of the differences ($\Sigma B$) between corresponding segments in the incoming complex and Normal B stored complex and generate a logic level Normal B Shape if $\Sigma B$ does not reach the Normal B threshold.

Further groups of sample/hold stages (Stores C, D, . . . etc.) may be used to store sets of segment areas representing additional previously stored waveform complexes Normal C, Normal D, . . . etc. For each such store further operational amplifiers calculate the sum of the magnitude of the differences $\Sigma C$, $\Sigma D$, . . . etc. and compare these with thresholds C, D, . . . etc. to generate logic levels Normal C Shape, Normal D Shape etc. whenever the shape of the incoming complex is sufficiently close to that of one of the stored Normal complexes.

When sufficient time has elapsed since the arrival of the complex for an adequate portion of its waveform to have been compared with the stored 'Normal' complexes, a 'decide' pulse is generated by the Control Section 13 and fed to the Logic section 14. Immediately before the generation of the decide pulse a pulse is fed from the Control Section 13 to the Timing Section 15 in which a linear time base waveform is sampled on the arrival of this pulse to produce a measure of the interval between the arrival of the incoming QRS wave and its predecessor. This interval is compared with a preset threshold (350 – 500 milli-seconds) and if this value is not reached a logic level 'early' is generated and fed to the Logic Section 14.

In the Logic Section 14 the logic voltage levels Foreign Shape, Normal A Shape, Normal B Shape, . . . etc. and early are combined on the arrival of the decide pulse to produce an output at one or more outputs corresponding to Normal A Complex, Early Normal C Complex, Foreign Complex, Early Foreign Complex . . . etc.

If a complex is found to be of one of the Normal shapes the Logic Section generates a corresponding Transfer Pulse ('Transfer A', 'Transfer B' . . . etc.) which is fed to the Operational Section 11 causing the sample/hold stages in the appropriate store A, B, . . . etc. to up-date their contents by sampling the contents of the integrators holding the current waveform samples. The integrators are subsequently reset to zero before the arrival of the next complex.

If the complex is not judged to be of any of the Normal Shapes no Transfer pulse is generated and none of the Stores is up-dated before the integrators are reset in readiness for the next complex.

The Inhibit Section 16 (FIG. 11) filters from the incoming e.c.g. signal the 'Baseline' signal used to correct the delayed e.c.g. on which shape measurements are made, and derives from the incoming signal both high frequency and low frequency noise components (shown as "HF", and "B.L.S." respectively) and feeds these to the Trigger Section 12 and Operational Section 11 where they are used as components of the adaptive trigger and shape thresholds. When any of the noise components accompanying the incoming signal exceeds its appropriate inhibit threshold, preset in the Inhibit Section 16, a logic level 'Inhibit' is fed to the Logic Section 14 inhibiting all decisions above Foreign or Normal shape etc. until the noise level subsides below the inhibit threshold.

When the system is put into operation on an e.c.g. signal an operator, observing the waveform on an oscilloscope or pen recorder (not shown), presses a push switch during the passage of an e.c.g. complex of the type he wishes the system to regard as Normal A. This switch injects a logic voltage level 'Learn A' into the Logic Section temporarily altering the way in which the various logic signals are combined so as to produce a transfer A pulse for every complex appearing while the switch is pressed. In this way the waveform of the desired Normal A e.c.g. complex is stored initially in the sample/hold stages of Store A in the Operational Section.

Similarly by pressing switches Learn B, Learn C etc. the operator can inject corresponding logic voltages into the Logic Section 14 so as to produce Transfer B, Transfer C, etc. pulses for any complex appearing while the corresponding switch is pressed. In this way the waveform of complexes of a number of different shapes can be stored in Stores B, C, . . . . etc.

The operation of individual sections of the system will now be considered in more detail.

The Delay Line

This may be as described in the complete specification of the main invention and as shown in FIG. 5. Referring to FIG. 5, the incoming signal is used to frequency modulate pulse generator 10a. The frequency modulated pulse train is fed to the input of a long chain of monostable circuits 10b to 10n arranged in cascade so that the trailing edge of the pulse produced by each monostable stage triggers the start of the pulse in the next monostable. The frequency modulated pulse train emerging from the last monostable in the chain is demodulated in a demodulator 10q to reproduce the original signal faithfully but with a time delay equal to the sum of the durations of the pulses produced by each monostable. Thus if 50 monostables are used each generating a 2msec pulse in turn the total delay is 100msec. Alternatively it may be of more conventional design comprising an analogue-to-digital convertor sampling the incoming e.c.g. signal at about 200 samples per second to produce a sequence of 8 bit digital numbers representing successive amplitudes of the signal. These digitised samples are fed into an eight bit parallel shift register and shifted down the line one place per sample. At the end of a shift register, say 100 bits long, the signal will emerge after a delay of 100 sampling periods i.e. 0.5 seconds in this case and enter an eight bit digital-to-analogue converter to re-emerge as a replica of the original e.c.g. signal delayed by 0.5 seconds.

Figure 8:
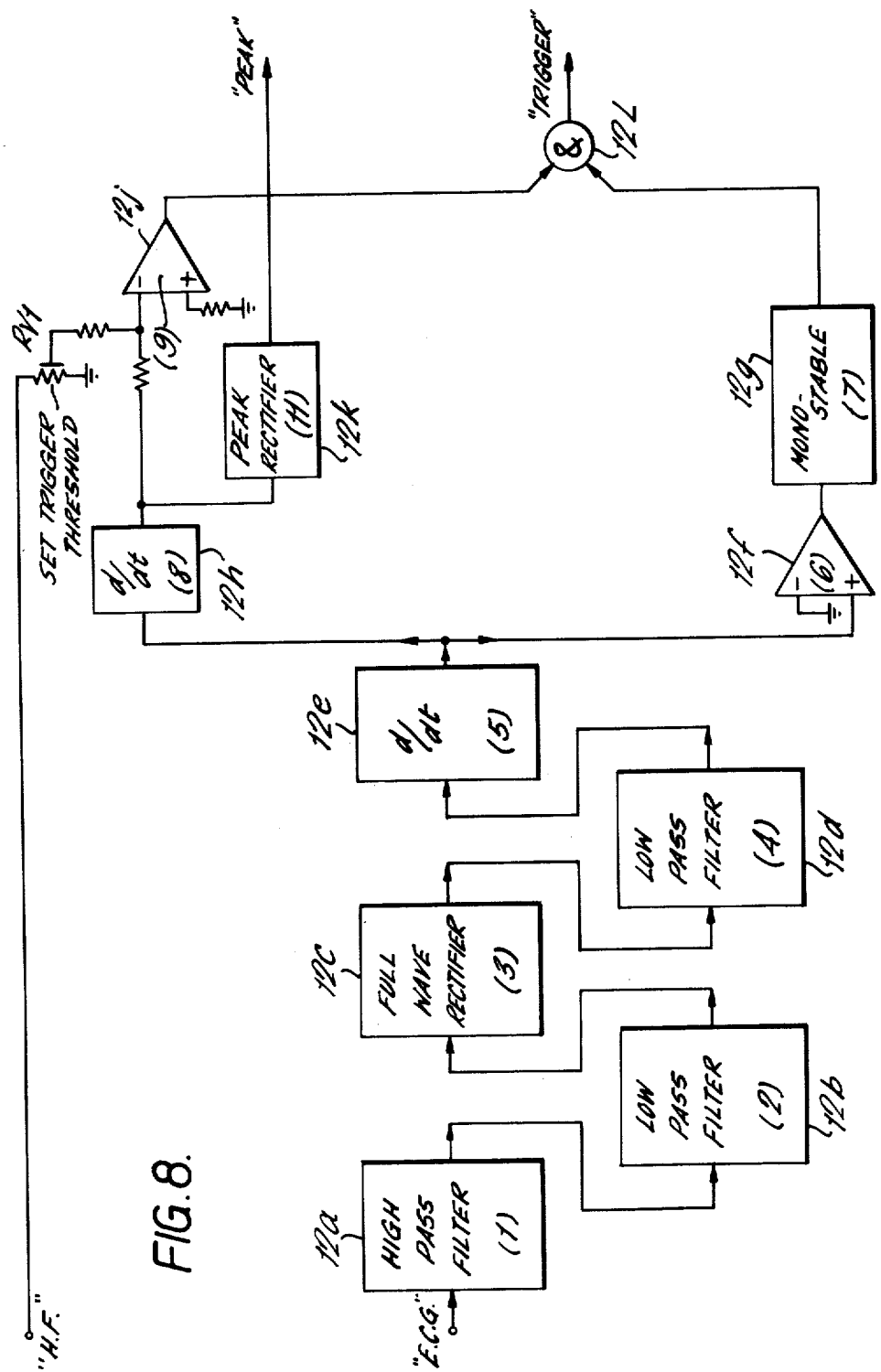
FIG. 8 shows an example of a trigger section suitable for use in FIG. 4.

The Trigger Section (FIG. 8)

This section of the invention detects the presence of individual complexes in the incoming e.c.g. signal by sensing the QRS wave in each complex and generating a Trigger Pulse on the occurrence of each QRS wave having a fixed time relationship to the middle of the period occupied by the QRS wave.

The incoming e.c.g. signal is passed through a high pass filter 12a and a low pass filter 12b. The time domain response of this filter combination is chosen to emphasise the QRS waves of a wide range of QRS waves relative to the p wave and T wave of the complexes and interference accompanying the signal. For example, the high pass filter 12a may have a sixth order critically damped response and a cut-off frequency of 5 Hz, and the low pass filter 12b may have a fourth order Butterworth response with a cut-off frequency of 10 Hz.

The output of filter 12b passes into a full wave rectifier 12c at the output of which each QRS wave produces a group of positive pulses which are fed to a low pass filter 12d. This low pass filter 12d smooths the envelope of the groups of pulses representing the QRS waves and has a time domain response chosen to optimise its response to groups of pulses originating in a wide range of QRS wave shapes and repetition rates and minimise the response to T waves and other interfering signals. For example it may have a sixth order critically damped response with a cut off frequency of 4 Hz. The output of low pass filter 12d is differentiated with respect to time in an operational amplifier differentiator 12e and the (inverted) differentiated signal is compared with zero volts level in an operational amplifier comparator 12f. The output of this comparator 12f triggers a monostable circuit 12g at each positive-going zero crossing of the differentiated signal emerging from differentiator 12e, that is at each maximum of the smoothed envelope waveform from low pass filter 12d. Each such maximum bears a fixed time relationship to the 'time centre' of a possible QRS wave so that monostable circuit 12g produces a pulse (which may be of 10 milliseconds duration) bearing a fixed time relationship to the centre of each possible QRS wave.

The output of differentiator 12e is also fed to another operational amplifier differentiator 12h the output of which is the second differential with respect to time of the smoothed envelope waveform at the output of low pass filter 12d. This twice differentiated waveform has a significant (negative) peak corresponding to each QRS wave in the incoming e.c.g. signal.

A comparator 12j compares the negative peaks with a preset fraction (set by a potentiometer $RV_1$) of the positive signal HF which is derived (in the Inhibit Section 16) from the mean high frequency (noise) components of the incoming e.c.g. signal. Each QRS wave produces a peak at the output of differentiator 12h exceeding the prevailing noise level represented by the signal HF results in a positive output from comparator 12j which is combined in a Logical AND-gate 12l with the output pulse from Monostable circuit 12g to produce an output pulse "TRIGGER" related in time to the centre of each QRS wave which significantly exceeds the prevailing noise level accompanying the e.c.g. signal.

A peak rectifier circuit 12k measures the peak amplitude of the negative peaks at the output of second differentiator 12h producing an output 'Peak' which represents the average amplitude of these peads excluding occasional larger peaks which may result from ventricular extrasystoles. (Details of this circuit's operation are described in the complete specification of British Pat. No. 1,282,051 page 4, lines 48–63).

Figure 11:
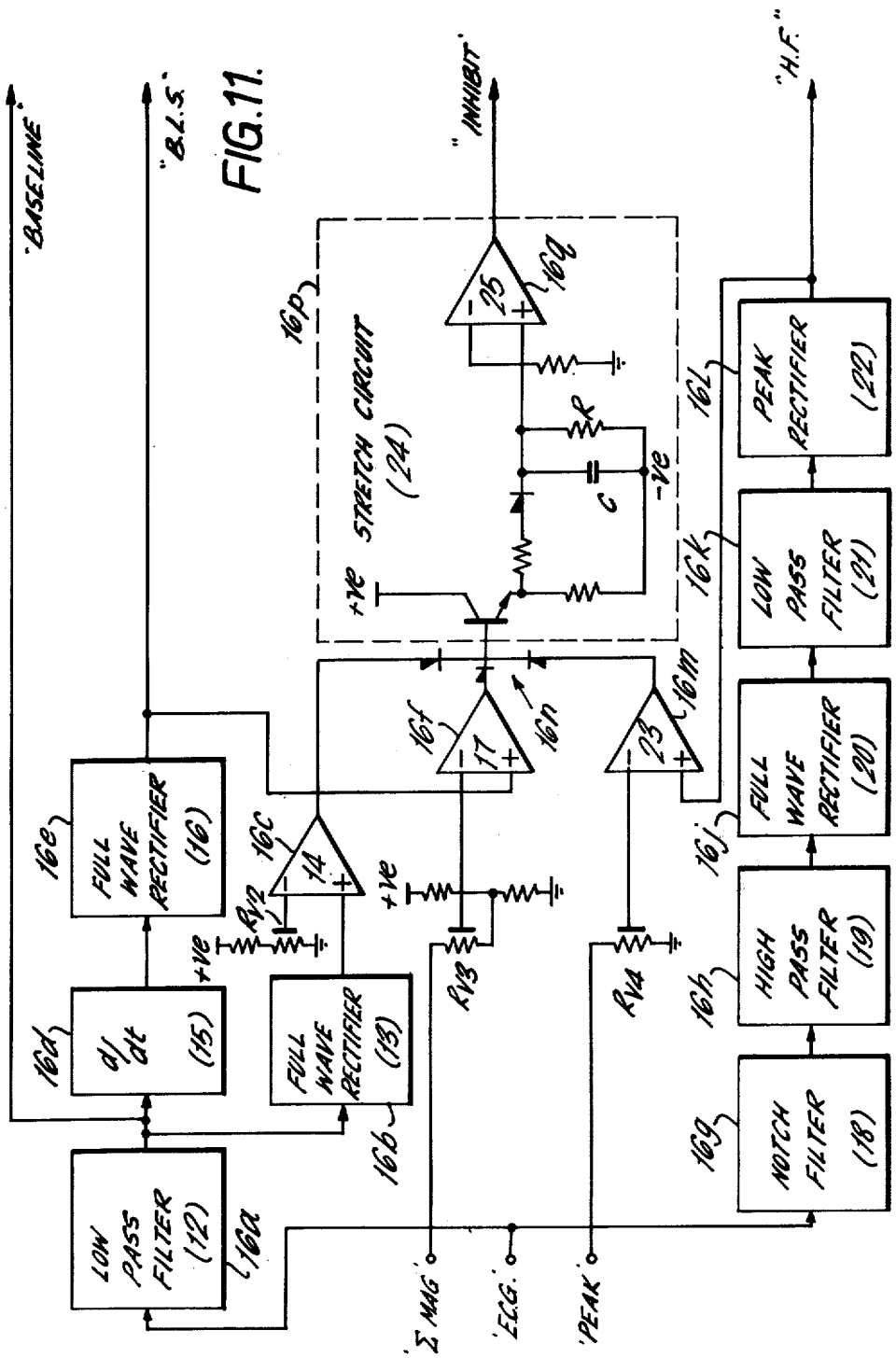
FIG. 11 shows an example of an inhibit section suitable for use in FIG. 4.

The Inhibit Section (FIG. 11)

The incoming e.c.g. signal is passed through a low pass filter 16a designed to eliminate from the signal all but the very lowest frequency components of the e.c.g. complexes leaving only a signal Baseline which is fed out from the Inhibit Section 16 to the Operation Section 11. This filter 16a may have a sixth order critically damped response with a cut-off frequency of 1.5 Hz. The Baseline signal is passed through a full wave rectifier 16b and compared with a preset voltage from a potentiometer $RV_2$ in a comparator 16c which produces a positive output whenever the baseline of the incoming signal deviates the zero volts by more than the threshold voltage set on $RV_2$. The Baseline signal is also passed through an operational amplifier differentiating circuit 16d and a full wave rectifier circuit 16e to produce a signal B.L.S. which is fed out from the Inhibit section 16 to the Operational Section 11. The signal B.L.S. is compared in a comparator 16f with a fraction (pre-set on potentiometer $RV_3$) of a signal Σ mag. representing the total area of the Normal A complex and obtained from the Operational Section 11. Should the signal B.L.S. representing the magnitude of the baseline slope exceed the preset fraction of Σ mag, comparator 16f produces a positive output.

Meanwhile the incoming e.c.g. signal is passed through a conventional notch filter 16g having a large attenuation at the mains supply frequency and a high pass filter 16L designed to have minimal response to most QRS waves but maximum response to high frequency interference (e.g. muscle potentials). This high pass filter 16h may have a fourth order Butterworth response with a cut-off frequency of 24 Hz.

The high frequency components of the incoming signal, less any component at supply mains frequency, are rectified by full wave rectifier 16j, smoothed by low pass filter 16k which may have a second order critically damped response and a cut-off frequency of 0.7 Hz, and passed through peak rectifier 16L to emerge as the signal HF which is fed out from the Inhibit Section 16 to the Trigger Section 12 and Operational Sections 11.

The signal HF is also compared in a comparator 16m with a fraction preset on $RV_4$ of the signal Peak from the Trigger Section 12. Should the signal HF representing the mean high frequency noise level of the incoming e.c.g. exceed the preset fraction of Peak which reflects the amplitude of the QRS waves, the comparator 16m produces a positive output.

The outputs of comparators 16c, 16f and 16m are combined in a diode OR network 16n and applied to a Stretch Circuit shown within a broken line 16p so arranged that positive signals from any of the three comparators will cause a capacitor C to be charged rapidly to the positive supply voltage producing a logic level "INHIBIT" at the output of comparator 16q. This logic signal will persist for a time which may be chosen to be about 500 milliseconds after the cessation of outputs from comparators 16c, 16f or 16m by suitable choice of the time constant of capacitor C and resistor R.

Figure 9:
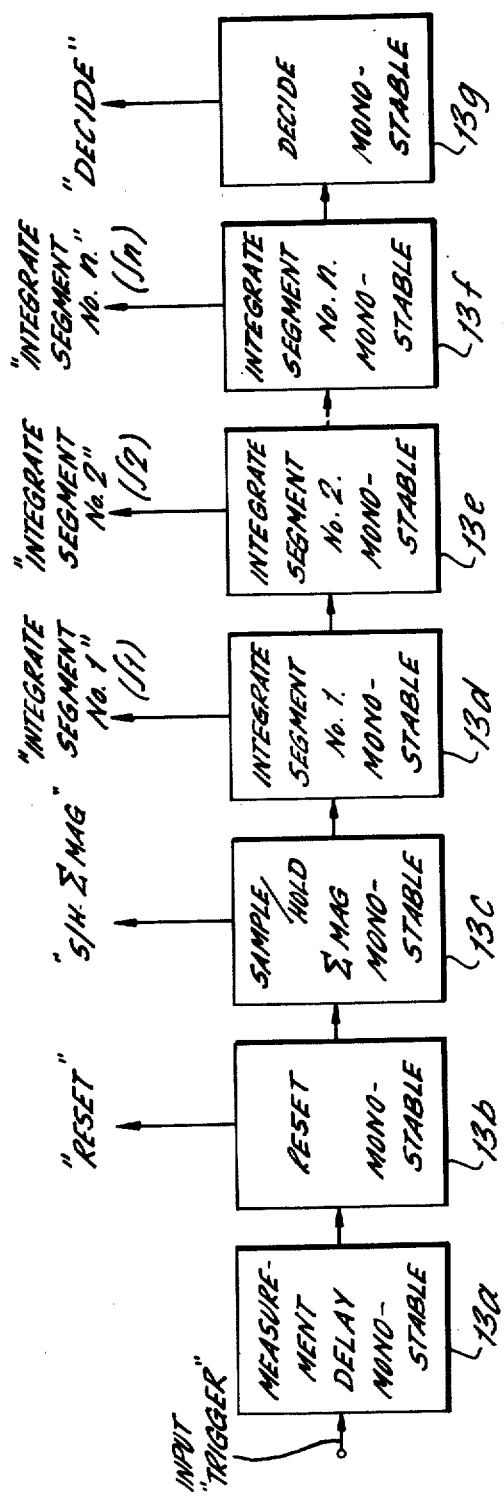
FIG. 9 shows an example of a control section suitable for use in FIG. 4.

The Control Section (FIG. 9)

The Trigger pulse from the Trigger section 12 operates a chain of monostable circuits 13a to 13g in which each monostable circuit in the chain is triggered by the trailing edge of the output pulse produced by the previous stage.

The incoming Trigger pulse operates a Measurement Delay monostable to which provides an output pulse of adjustable duration so that the pulses from subsequent monostable circuits in the chain can be arranged to occur in the desired time relation to the delayed QRS wave entering the Operational Section 11.

The trailing edge of the output pulse from the Measurement Delay monostable circuit 13a triggers a Reset monostable circuit 13b which produces an output pulse 'Reset' used to reset to zero the set of sampling integrators in the Operational Section 11. The trailing edge of the Reset pulse operates the 'Sample/Hold $\Sigma$ Mag' monostable circuit 13a which produces a pulse 'S/H $\Sigma$ Mag'used to sample the sum of the magnitude of the difference signals in the Operational Section 11.

The trailing edge of the S/H $\Sigma$ Mag pulse is used to trigger a monostable circuit 13d producing an output pulse 'Integrate Segment No. 1' at a time adjusted to be at or just before the arrival of the delayed QRS wave at the input to the Operational Section 11. The end of Integrate Segment No. 1 pulse triggers the next monostable circuit 13e to produce Integrate Segment No. 2 pulse, and so on down the chain each monostable circuit operating a corresponding Integrator in the Operational Section 11. The Integrators each run for the duration of their command pulses (preferably a multiple of 20 milliseconds when the AC mains frequency is 50 Hz), then revert to their 'hold' mode.

When sufficient segments of the delayed e.c.g. complex have thus been sampled, the trailing edge of the last Integrate Segment No. $n$ monostable circuit 13f triggers a monostable circuit 13g producing the Decide pulse which is fed to the Logic Section.

Figure 6:
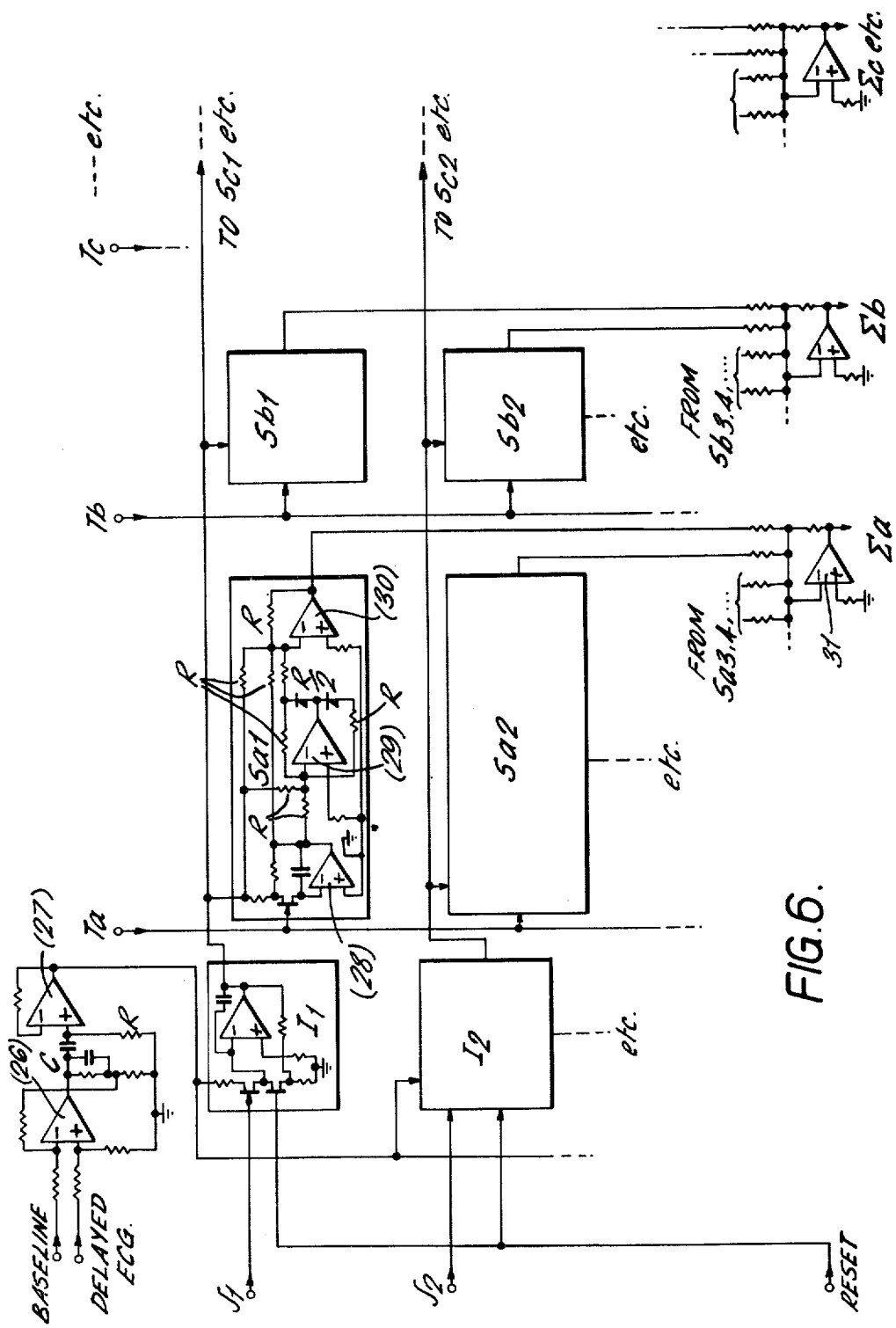
FIGS. 6 and 7 show one example of an operational section suitable for use in FIG. 4.
Figure 7:
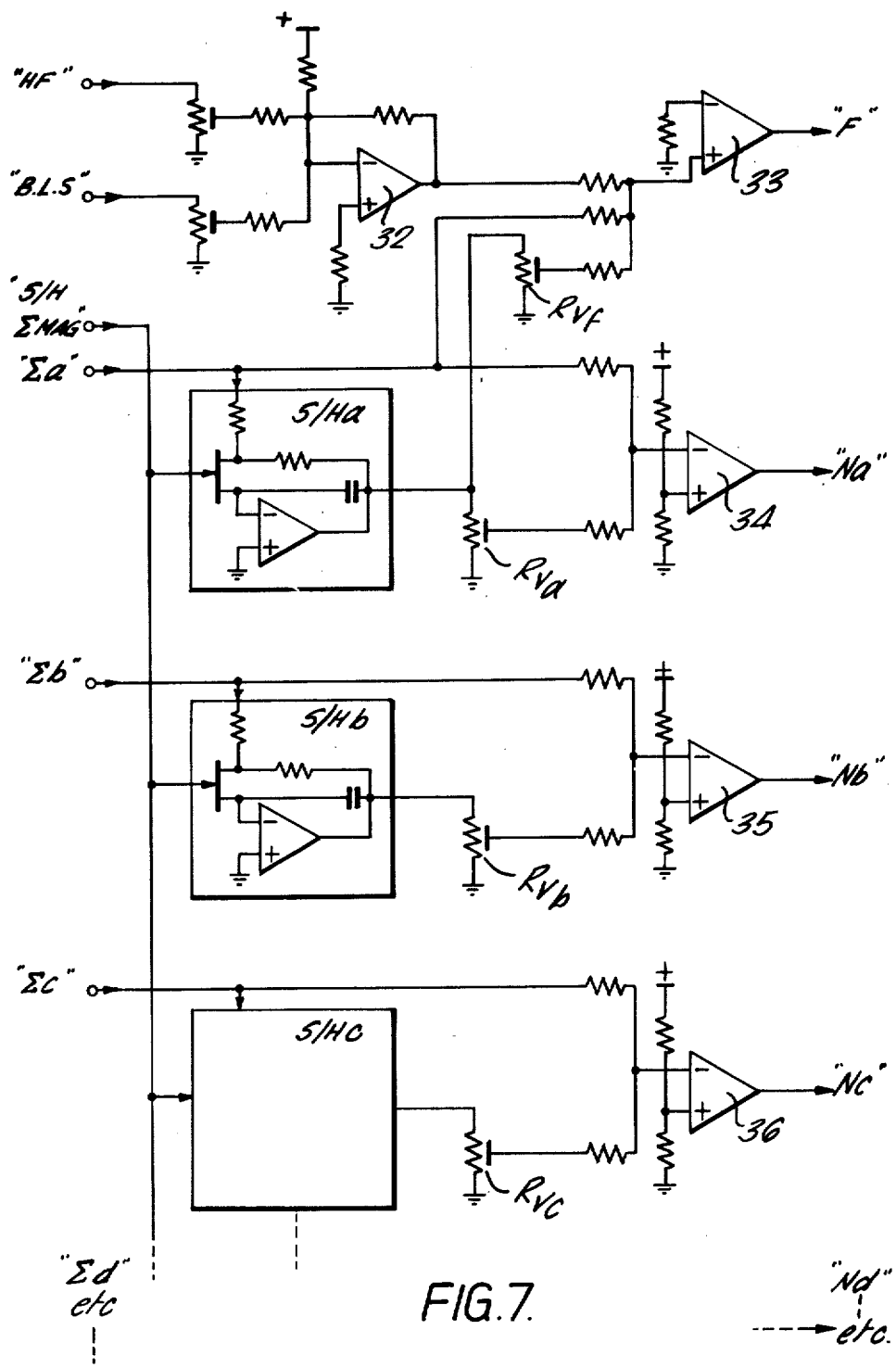

The Operational Section (FIGS. 6 and 7)

The essential features of the Operational Section developed to handle a number of separate Normal waveform complexes are shown in FIGS. 6 and 7. In FIG. 6 the Baseline signal from the Inhibit Section 16 is subtracted from the Delayed e.c.g. signal in a differential amplifier stage 26. Further attenuation of any remaining baseline variation is provided by a high pass network CR and the resulting corrected (delayed) e.c.g. signal fed through buffer amplifier 27 to the Sampling Integrator Stages $I_1, I_2 \ldots I_n$.

Shortly before the arrival at the Operational Section 11 of each QRS wave detected by the Trigger Section 12 a Reset pulse from the Control Section 13 resets all of the Integrators $I_1, I_2 \ldots$ etc. to zero. Thereafter, as the delayed QRS wave enters the Operational Section 11 command pulses Integrate Segment No. 1 ($\int 1$), Integrate Segment No. 2 ($\int 2$), Integrate Segment No. $n$ ($\int n$) from the Control Section 13 cause each integrator in turn to acquire at its output a voltage representing the average value of the delayed QRS waveform during the time segment bounded by the start and finish of the appropriate command pulse. After each command pulse the integrator concerned reverts to its hold mode and maintains this sample of the average voltage in its segment of the QRS wave at its output. Preferably the number and duration of these measurement segments is chosen so that the period from the start of the first measurement segment to the end of the last extends from before the earliest start of any QRS wave to well after the end of the widest QRS wave expected.

The output of sampling Integrator $I_1$ is fed to Store Circuit $Sa_1$ which contains a Sample/hold stage 28 which, on command of Transfer A pulse (T$a$), samples and holds the voltage then present at the output of Integrator $I_1$, and further stages 29, 30 which derive the magnitude (absolute value) of the difference between the incoming signal from $I_1$ and the voltage held in the sample/hold stage 28. Similarly the outputs of Integrators $I_2, I_3, \ldots I_n$ are connected each to its own Store Circuit $Sa_2, Sa_3 \ldots Sa_n$.

The outputs of this (A) set of stores are added together in a summer 31 to form the signal $\Sigma a$, the sum of the magnitudes of the differences between the set of samples of the current e.c.g. complex held at the outputs of Integrators $I_1 \ldots I_n$ and the set of samples of the Normal (a) e.c.g. complex held in the sample/hold stages 28 of the set of store circuits $Sa_1 \ldots Sa_n$.

The outputs of the set of Integrators $I_1, \ldots I_n$ are also connected to a set of store circuits $Sb_1 \ldots Sb_n$ holding a set of samples representing Normal (b) complex and developing at the output of the (B) store set a sumed voltage $\Sigma$ (b) representing the sum of the magnitudes of the differences between the set of samples of the current e.c.g. complex and a set of samples of Normal (b) e.c.g. complex.

Further sets of Store Circuits $Sc_1 \ldots Sc_n$ etc. may be provided yielding $\Sigma(c)$ etc. signals representing the difference in shape between the current complex and any desired number of stored Normal complexes.

FIG. 7 shows the part of the Operational Section 11 concerned with the comparison of the various 'Sum of the magnitudes of the differences' signals $\Sigma a, \Sigma b, \Sigma c$ etc. with adaptive thresholds to determine whether the incoming complex is to be classed as Normal $a$, Normal $b, \ldots$ etc., or Foreign. The command pulse S/H Mag causes the set of sample/hold stages S/H$a$, S/H$b \ldots$ etc. to sample and hold the current value of their respective inputs $\Sigma a, \Sigma b, \Sigma c \ldots$ etc. Each of these stages then holds at its output a (negative) voltage ($\Sigma$Mag. $a$, $\Sigma$Mag. $b, \ldots$ etc.) proportional to the total area of its stored Normal complex. The signals HF and B.L.S. representing the prevailing noise accompanying the incoming e.c.g. signal are combined in preset proportions with a fixed DC voltage in a summer 32. The (negative) sum so formed is combined with a (negative) fraction (preset on RV$_F$) of $\Sigma$Mag.a and the (positive) signal $\Sigma a$ representing the difference in shape between the incoming complex and the stored Normal $a$ complex. The combined signal is fed to a comparator 33 which produces a logic voltage level "F" whenever the postive signal $\Sigma a$ exceeds the threshold formed by the (negative) combination of HF, B.L.S., $\Sigma$Mag a and the DC term.

At the same time, the positive signal $\Sigma a$ is compared in a comparator 34 with a negative threshold formed by another fraction of $\Sigma$Mag $a$ preset on RV$_a$ and a DC voltage. Comparator 34 produced a logic voltage level N$a$ whenever $\Sigma a$ is smaller in amplitude than this preset Normal $a$ threshold. Likewise comparators like 35 and 36 and so on produce logic levels N$b$ and N$c$ etc. whenever their respective inputs $\Sigma b, \Sigma c$, etc are smaller in amplitude than the corresponding Normal thresholds set on $RV_b$, $RV_c$ etc. The logic voltage levels F, $Na$, $Nb$, $Nc$ ... etc. generated by this circuit in the Operational Section 11 are fed to the Logic Section 14 where they are strobed by the Decide pulse from the Control Section 13 immediately after the sampling of successive segments of the incoming complex to determine whether this complex is to be classed as Normal $a$ Shape, Foreign Shape, or Normal $b$ Shape etc.

Figure 10:
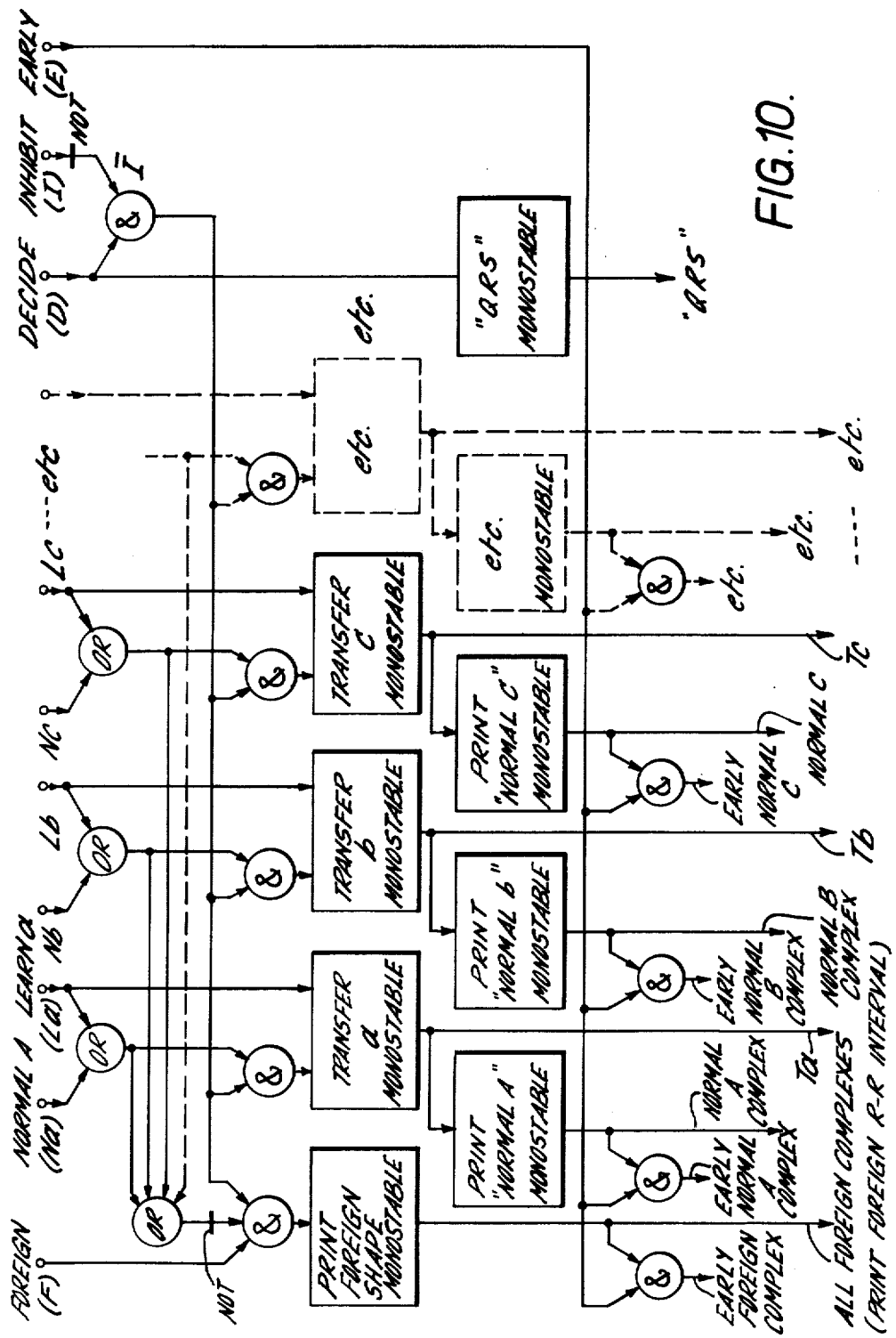
FIG. 10 shows an example of a logic section suitable for use in FIG. 4.

The Logic Section (FIG. 10)

FIG. 10 shows one arrangement of electronic logic elements and monostable circuits which may be used to combine the logic levels Foreign Shape (F), Normal $a$ Shape ($Na$), Normal $b$ Shape ($Nb$), Early (E), Decide (D), Learn A ($La$), Learn B ($Lb$), etc. to obtain the correct function of the system generating Command pulses Transfer $a$ ($Ta$), Transfer $b$ ($Tb$), etc. and a variety of outputs such as Foreign Complex, Early Foreign Complex, Normal $a$ Complex, Early Normal $b$ Complex, etc. Other arrangements are possible. Some of the logic levels are passed through logic 'Not' elements to generate logic signals representing Not Inhibit (I) etc. These signals and the incoming ones are combined in AND and OR gates as shown to Trigger Monostable circuits generating Transfer A, Transfer B etc. and any desired Print-Out signals. In addition to the outputs illustrated many other outputs may be ontained from the system by arranging Print-Out signals from the Logic Section to operate electronic switches to sample and feed out any of the waveforms present in any chosen section of the system. For example a pulse whose amplitude represents the time interval between the QRS wave of each Foreign complex detected and the previous QRS wave can be obtained by arranging the Foreign Complex output to sample the current inter-QRS wave interval being held in the Sample/Hold store in the Timing Section.

So that the shape of a selected Normal Complex may be learnt by the system, given just one example of the complex, the logic levels Learn A, Learn B etc. are fed to electronic switches in the corresponding Transfer A, Transfer B . . Monostables causing the monostable concerned to generate a Transfer pulse of extended duration when the Learn logic level is present.

Figure 12:
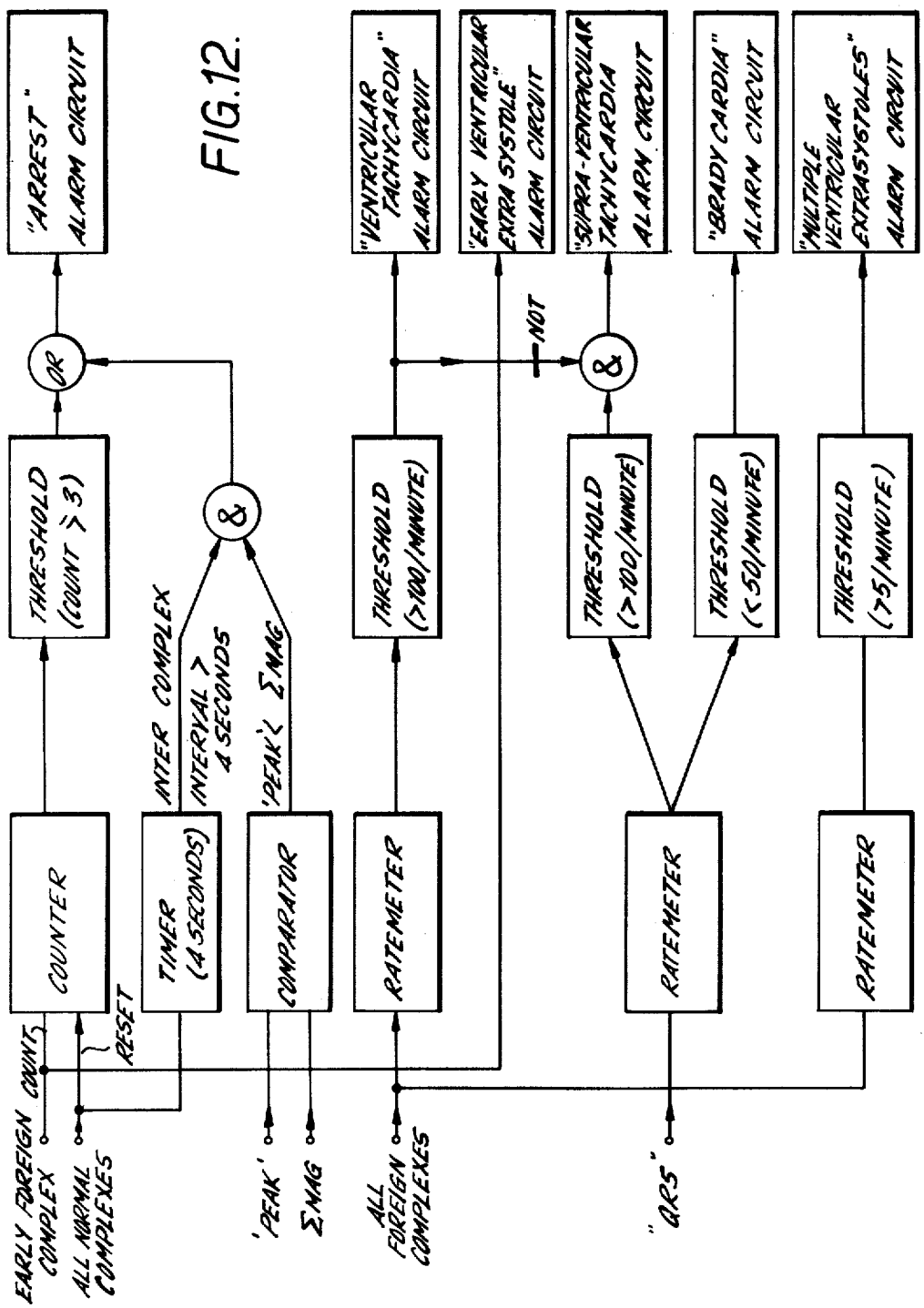
FIG. 12 shows an example of an alarm section suitable for use in FIG. 4.

Alarm Section (FIG. 12)

The system as described so far is capable of recognising on line the broad categories into which individual e.c.g. complexes fall viz.; Normal ($a$, $b$, $c$ etc.), Foreign, Early, etc. and combinations of these. In a developement of the invention, its range and performance can be extended to diagnose automatically certain well known disturbances of heart rhythm characterised by the occurrence of particular types of complex at certain rates and to warn operator by means of alarms specific to the rhythm disturbance detected.

FIG. 12 shows one possible arrangement of conventional ratemeters, timers, threshold comparators and logic gates which may be used to distinguish separately six different rhythm disturbances.

Figure 13:
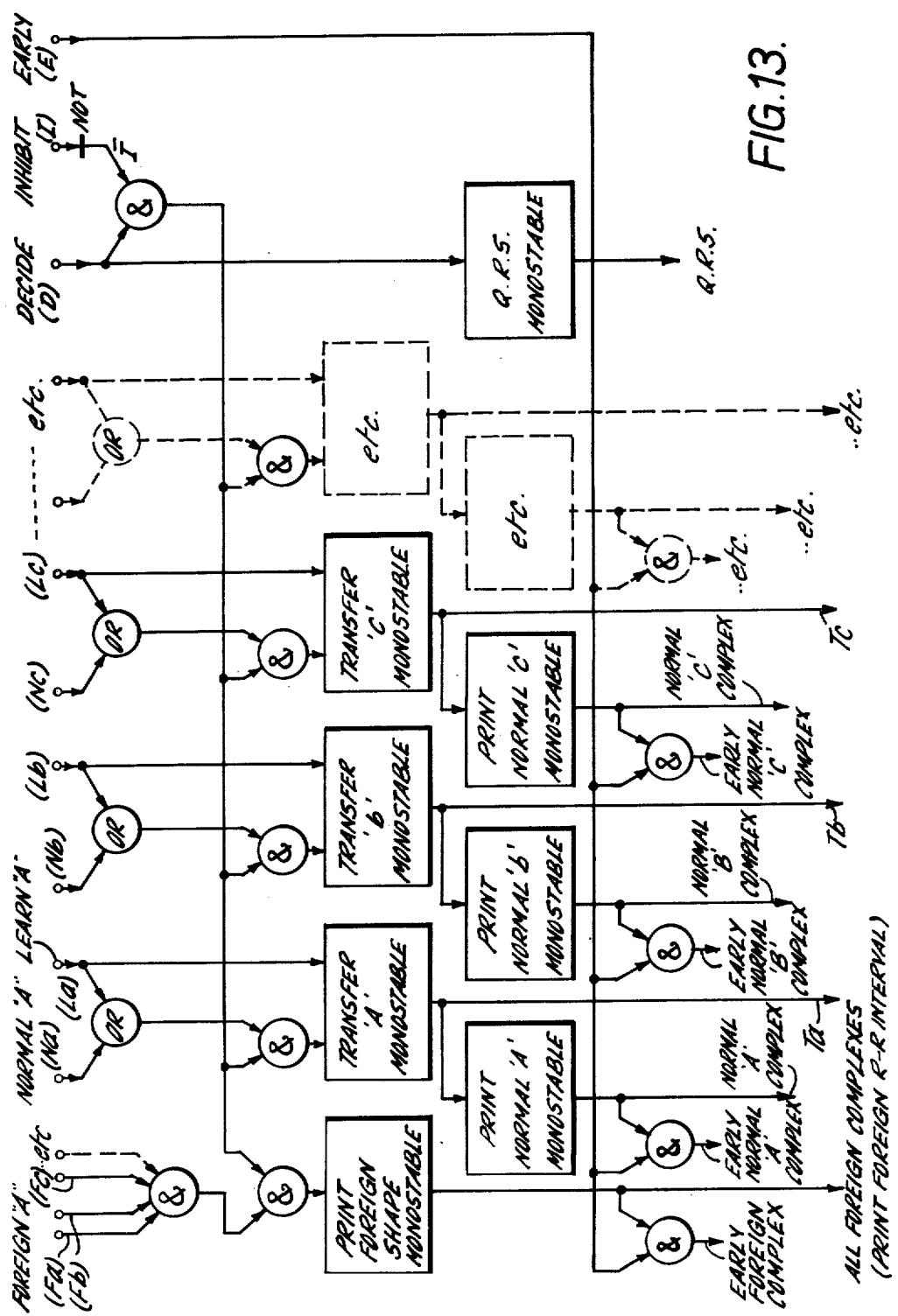
FIG. 13 shows an example of another logic section suitable for use in FIG. 4.

FIG. 13 shows an alternative logical arrangement for defining a system output indicating a foreign complex requires that there be a separate foreign threshold for each of the stored normal complexes.

The system will produce an output indicating a foreign complex only when this incoming complex is sufficiently different from all of the stored normal complexes. That is, when $\Sigma_A > T_{FA}$ AND $\Sigma_B > T_{FB}$ ($T_{FA}$ and $T_{FB}$ are foreign thresholds respectively of complex A and complex B) AND ... $\Sigma_{(p+1)} > T_{F\ (p+1)}$; so that logic signals $T_{FA}$, AND $T_{FB}$ .... AND $F_{(p+1)}$ are present together. This condition is necessary and sufficient for a foreign complex to be identified since clearly the incoming complex cannot then be Normal with respect to any of the stored complexes.

As before if $\Sigma_A < T_{NA}$, OR $\Sigma_B < T_{BN}$, OR ... $\Sigma p + 1 < T_{N\ (p+1)}$ that is the incoming signal is a sufficiently good match to any one (or more) of the stored normal complexes, an output (or outputs) will be generated indicating with which Normal complex (or complexes) a match has been obtained.

Each of the ($p + 1$) separate foreign thresholds are generated by combining in predetermined proportions, signals proportional to the area of *the corresponding stored normal complex:* to the high and low frequency contents of the incoming signal to be monitored and a fixed D.C. level.

The necessary apparatus would employ ($p + 1$) separate Foreign Comparators (like 33 FIG. 7) each fed from summer 32 and its own total area signal from the corresponding $S/H_a$, $S/H_b$ .... stage.

I claim:

1. A method of monitoring a recurrent waveform to detect abnormal waveform complexes comprising the steps of integrating successive segments of a waveform complex, determining the difference between the integrated value of each segment in the complex and the integrated values of corresponding segments of ($p + 1$) different normal waveform complexes, where $p$ is an integer, to provide ($p + 1$) sets of difference signals, quantitatively summing the difference signals associated with each normal waveform and producing a signal and/or record to indicate an abnormal complex if the total sum of the magnitudes of the difference signals associated with a first normal waveform complex exceeds a first threshold level and the sums of the magnitudes of the $p$ other difference signals are not less than a second threshold level for each of the $p$ other normal waveform complexes.

2. A method according to claim 1, in which the threshold levels are the same.

3. A method according to claim 1, in which the threshold levels are adaptive and including deriving said adaptive threshold levels from variables.

4. A method according to claim 1, further comprising the step of producing a second signal and/or record if one of the sums of the magnitudes of the difference signals is less than its associated threshold level, and arranging the second signal and/or record to indicate that the monitored waveform is a normal waveform and to which of the ($p + 1$) normal waveforms it corresponds.

5. A method according to claim 3 in which said deriving of threshold levels from variables includes deriving each threshold level from a voltage dependent upon the total area of the corresponding normal complex, the variable high frequency and low frequency contents of the signal to be monitored, and a fixed, d.c. level.

6. A method according to claim 1, including simultaneously determining the difference between the integrated value of each segment in the complex of the waveform to be monitored and the corresponding segments of each of the ($p + 1$) normal waveforms.

7. A method according to claim 1 including also producing a signal and/or record to indicate an abnormal complex if the sum of the magnitudes of the difference signals associated with all of the normal waveform complexes exceed threshold values.

8. A method according to claim 1, further comprising the step of producing further a signal and/or record if one or more of the sums of the magnitudes of the difference signals is less than another associated (such as Normal threshold) threshold level, and arranging the latter signal and/or record to indicate that the monitored waveform is a normal waveform and to which of the $(p + 1)$ normal waveforms it corresponds.

9. A method of monitoring a recurrent waveform to detect abnormal waveform complexes comprising the steps of integrating and storing segments of a normal waveform complex to be used as a reference, integrating successive segments of a waveform complex, deriving timing signals from the recurrent waveform wherein the timing signals represent the time location of particular selected parts of the waveform complex required to be compared with the integrated value of corresponding parts of the stored normal complex, deriving a correcting signal by filtering the waveform to be monitored by passing it through a low-pass filter to provide a baseline signal, delaying the waveform, subtracting said correcting signal from said delayed waveform to provide a corrected waveform, determining, with the aid of the timing signals, the difference between the integrated value of each segment in the corrected complex and the integrated value of a corresponding segment of the normal waveform complex to provide a difference signal, quantitatively summing the difference signals and producing a signal and/or record if the total sum of the magnitudes of the difference signals exceed a predetermined value to indicate an abnormal complex.

10. A method according to claim 9, including filtering the corrected waveform by passing it through a high-pass filter before the step of determining the difference between the integrated value of each segment in the corrected complex and the integrated value of a corresponding segment of the normal waveform.

11. A method according to claim 9, in which the timing signals are derived from the recurrent waveform by high-pass filtering, rectifying, smoothing and differentiating twice the smoothed signal in that order, and comparing the resulting second derivative signal with a threshold derived by separately high-pass filtering and smoothing the high frequency noise components of the recurrent waveform to be monitored to provide an output signal when the second derivative signal exceeds the threshold signal.

12. A method according to claim 11, in which the step of twice differentiating also provides a first derivative signal, and including comparing said first derivative signal with a reference level (such as zero volts) to provide a signal when it is equal to the reference level, applying the latter signal to a monostable circuit for generating at its output a pulse of predetermined time duration and having a fixed time relationship to the centre of that part of the waveform complex to be compared with the reference complex, and adding said output signal, generated when the second derivative signal exceeds the threshold signal, to the pulse from the monostable circuit in an AND-gate to provide a trigger signal, said trigger signal being said timing signal.

13. A method according to claim 12, in which the integration of corresponding segments of each normal waveform complex to be stored, and the waveform complex to be compared with it is successive and including carrying out said integration by operational amplifiers electronically switched under the control of the timing signal.

14. A method according to claim 13, including arranging the operational amplifier stages to obtain the differences between each integrated segment of the waveform complex and that of each stored reference waveform complex and to obtain the sums of the magnitudes of said individual differences over a time interval including the start of the waveform complex and the end of the widest expected waveform complex.

15. Apparatus for monitoring recurrent waveforms to detect abnormal waveform complexes in said recurrent waveform comprising means for integrating successive segments of a waveform complex, means for determining the difference between the integrated value of each segment in the complex and the integrated values of the corresponding segments of $(p + 1)$ different normal waveform complexes, where $p$ is an integer, to provide $(p + 1)$ sets of difference signals, means for adding the magnitudes of said difference signals associated with each normal waveform irrespective of sign, and means for indicating an abnormal complex if the total sum of the magnitudes of the difference signals associated with a first normal waveform complex exceeds a first threshold level and the sums of the magnitudes of the $p$ other difference signals are not less than a second threshold level for each of the $p$ other normal complexes.

16. Apparatus according to claim 15, further comprising means for indicating a normal complex if one of the sums of the magnitudes of the difference signals is less than an associated threshold level and for indicating to which of the $(p + 1)$ normal waveforms it corresponds.

17. Apparatus according to claim 15, in which the threshold levels are the same.

18. Apparatus according to claim 15, in which the threshold levels are adaptive and including means for deriving said thresholds from variables of the incoming complex to be monitored.

19. Apparatus according to claim 18 in which said means for deriving includes means producing each threshold level from a voltage dependent upon the total area of the corresponding normal complex, the high frequency and low frequency contents of the signal to be monitored and a fixed, d.c. level.

20. Apparatus according to claim 15, in which said means for determining the difference between the integrated value of each segment in the complex of the waveform to be monitored and the corresponding segments of the $(p + 1)$ normal waveforms include parallel means for carrying out said determinations simultaneously.

21. Apparatus according to claim 15, in which the indicating means includes means for providing an indication of an abnormal complex if the sums of the magnitudes of the difference signals associated with all of the normal waveform complexes exceed threshold values.

22. Apparatus for monitoring a recurrent waveform to detect abnormal waveform complexes comprising means for integrating and storing segments of a normal waveform complex to be used as a reference, means for integrating successive segments of a waveform complex to be monitored, means for timing signals from the recurrent waveform wherein the timing signals represent the time location of particular selected parts of the waveform complex required to be compared with the integrated value of corresponding parts of the stored normal complex, means for deriving a correcting signal, including means for filtering the waveform to be monitored by passing it through a low-pass filter to provide a baseline signal, means for delaying the waveform, means for subtracting said correcting signal from said delayed waveform to provide a correct waveform, means for determining, with the aid of the timing signals, the difference between the integrated value of each segment in the corrected complex and the integrated value of a corresponding segment of the normal waveform complex to provide a difference signal, means for quantitatively summing the difference signals and for producing a signal and/or record if the total sum of the magnitudes of the difference signals exceed a predetermined value to indicate an abnormal complex.

23. Apparatus according to claim 22, further comprising means for passing the corrected waveform through a high-pass filter to the means for determining the difference between the integrated value of each segment in the corrected complex and the integrated value of a corresponding segment of the normal waveform.

24. Apparatus according to claim 22, in which the means for deriving timing signals comprises a high-pass filter, a rectifier, smoothing means, means for differentiating twice the smoothed signal coupled together in that order, and means for comparing the second derivative signal with a threshold level derived by a high-pass filter and smoothing means for filtering and smoothing the high frequency noise components of the recurrent waveform to be monitored to provide an output signal when the second derivative signal exceeds the threshold signal.

25. Apparatus according to claim 23, in which the means for deriving timing signals comprises means for comparing the first derivative signal, resulting from said differentiating twice, with a reference level (such as zero volts) to provide a signal when it is equal to the reference level, and for applying the signal to a monostable circuit for generating at its output a pulse of predetermined time duration and having a fixed time relationship to the centre of that part of the waveform complex to be compared with the reference complex, and means for adding the output signal generated when the second derivative signal exceeds the threshold signal to the pulse from the monostable circuit in an AND-gate to provide a trigger signal, said trigger signals being said timing signals.

26. Apparatus according to claim 25, in which the integration of corresponding segments of the or each normal waveform complex to be stored and the waveform complex to be compared with it is successive and carried out by operational amplifiers electronically switched under the control of the timing signal.

27. Apparatus according to claim 26, in which the operational amplifier stages are arranged to obtain the differences between each integrated segment of the waveform complex and the or each stored reference waveform complex and to obtain the sums of said individual differences over a time interval including the start of the waveform complex and the end of the widest expected waveform complex.

28. Apparatus according to claim 22 in which said recurrent waveform is a series of e.c.g. waveforms, in which the indicating means is arranged to record and/or indicate different disturbances of the heart rhythm of a patient, including ventricular tachycardia, and including individual alarms specific to the condition detected.

29. Apparatus according to claim 15 in which the threshold levels are different.

30. Apparatus for monitoring a series of incoming waveform complexes, normally having a predominant peaked portion, to detect abnormal complexes, comprising:
  delay means for delaying an incoming waveform complex; trigger means including
  i. a first trigger path receiving said incoming complex and comprising a high pass filter, a low pass filter, a full wave rectifier, a low pass filter and a first derivative circuit,
  ii. a second trigger path serially following said first path and comprising means providing a second derivative signal, a comparator actuable when said second derivative signal exceeds a high frequency noise threshold and an AND-gate in series, said second derivative signal causing a peak signal, at the peak of said peaked portion, through a peak rectifier,
  iii. a third trigger path paralleling said second path and comprising means comparing the second differential signal to a reference level, monostable means triggered thereby at the zero crossing of the second derivative signal, and said AND-gate, said AND-gate being responsive to coincidence of outputs from said second and third paths for producing a trigger signal time related to the center of each incoming complex's peaked portion which significantly exceeds the high frequency noise level in such complex; and
  inhibit means including
  i. low pass filter means responsive to said incoming complex for providing a baseline signal,
  ii. first derivative and rectifier means responsive to said baseline signal for providing a baseline slope signal,
  iii. rectifier and comparator means providing a signal when said baseline signal exceeds a threshold level,
  iv. means responsive to a selected fraction of the total area of one stored normal complex exceeding the baseline slope signal for also providing a signal,
  v. means also providing a signal when the mean high frequency noise level of the incoming complex exceeds a preselected fraction of said peak signal,
  vi. stretch circuit means responsive to a said signal from (iii), (iv) or (v) above for providing an inhibit signal,
  vii. a series path including a notch filter means, high pass filter, rectifier, low pass filter and peak rectifier for signaling said mean high frequency noise level and means applying a corresponding signal to (v) above and to said second trigger path comparator.

31. The apparatus of claim 30 further including:
  control means responsive to said trigger signal for providing a series of n timed control signals;
  operational means responsive to said timing signals and including
  i. a series differential amplifier and high pass filter means responsive to said baseline signal and delayed complex for providing a time delayed, level corrected version of said incoming complex;

ii. n integrator means responsive to corresponding said timing signals for integrating n successive signals of said corrected incoming complex from (i) above, iii. $p + 1$ sets of n store circuits, each store circuit including means for storing an $n^{th}$ segment of a corresponding one of $p + 1$ different normal complexes and means for taking the absolute value of the difference between the integrated values of a corrected incoming complex segment and a corresponding stored normal complex segment, and $p + 1$ sum means for summing said difference absolute values for the corresponding one of said $p + 1$ store circuit sets to provide $p + 1$ sum signals, iv. abnormal signal means responsive to a said sum signal from (iii) above exceeding an adaptive threshold, comprising a preselectable function of said mean high frequency noise level and said baseline slope signal and a preset D.C. level and the sum of integrated segments of one said stored normal complex, for producing an abnormal logic signal, v. $p + 1$ normal signal means, each responsive to a corresponding one of said $p + 1$ sum signals from (iii) above less than a selected function of the sum of the integrated segments of a corresponding one of said $p + 1$ stored normal complexes, for producing a corresponding one of $p + 1$ normal logic signals, timing means responsive to said control means for indicating by an early signal that said peaked portion of said incoming complex is earlier in the complex than normal;

logic means responsive to i. said abnormal signal for indicating that the incoming complex is abnormal and to a said early signal for further indicating the incoming complex is an early abnormal complex, ii. said $p + 1$ normal signals and for indicating the incoming complex corresponds to the closest one of said $p + 1$ stored normal complexes and additionally responsive to occurrence of a said early signal for indicating the incoming complex corresponds to an early version of said one stored normal complex, and including means responsive to said indication in (ii) above that the incoming complex corresponds to a said stored normal complex for updating the corresponding said set of $n$ store circuits with said incoming complex prior to processing of a new incoming complex; and alarm means responsive to said indications from said logic means for actuating the appropriate one of several alarms each indicative of a different abnormality.

32. The apparatus of claim 31 wherein said logic means includes means responsive to coincidence of an abnormal signal and no normal signals for so indicating the incoming complex abnormal.

33. The apparatus of claim 31 wherein said operational means includes at least one said abnormal signal means for a given one of said $p + 1$ stored normal complexes, and said logic means includes means requiring coincident outputs from all said abnormal signal means for so indicating the incoming complex is abnormal.

* * * * *